(12) United States Patent
Fukamachi et al.

(10) Patent No.: US 8,983,601 B2
(45) Date of Patent: Mar. 17, 2015

(54) EXTRAVASCULAR NEUROMODULATION TO TREAT HEART FAILURE

(75) Inventors: Kiyotaka Fukamachi, Mayfield Heights, OH (US); Alex Massiello, Chesterland, OH (US); Mariko Kobayashi, Cleveland, OH (US); Ray Dessoffy, Parma, OH (US); Eugene Jung, Beachwood, OH (US); Shubhayu Basu, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 230 days.

(21) Appl. No.: 13/405,909

(22) Filed: Feb. 27, 2012

(65) Prior Publication Data

US 2012/0221072 A1 Aug. 30, 2012

Related U.S. Application Data

(60) Provisional application No. 61/513,373, filed on Jul. 29, 2011, provisional application No. 61/446,708, filed on Feb. 25, 2011.

(51) Int. Cl.
*A61N 1/00* (2006.01)
*A61N 1/36* (2006.01)
*A61N 1/362* (2006.01)

(52) U.S. Cl.
CPC ........ *A61N 1/36114* (2013.01); *A61N 1/36139* (2013.01); *A61N 1/3627* (2013.01)
USPC .................................. 607/9; 607/17; 607/18

(58) Field of Classification Search
CPC ............ A61N 1/36114; A61N 1/3627; A61N 1/36053
USPC ................................................ 607/9, 17, 18
See application file for complete search history.

(56) References Cited

U.S. PATENT DOCUMENTS

| 7,112,219 | B2 | 9/2006 | Vidlund et al. |
| 2007/0299476 | A1* | 12/2007 | Park et al. .......................... 607/9 |
| 2008/0228252 | A1 | 9/2008 | Westlund et al. |
| 2009/0171411 | A1 | 7/2009 | Machado et al. |
| 2009/0248119 | A1* | 10/2009 | Libbus et al. ................... 607/62 |

OTHER PUBLICATIONS

Meyer et al., Augmentation of Left ventricular Contractility by Cardiac Sympathetic Neural Stimulation, Circulation (Mar. 23, 2010), pp. 1286-1294.

* cited by examiner

*Primary Examiner* — Christopher D Koharski
*Assistant Examiner* — Philip Edwards
(74) *Attorney, Agent, or Firm* — Tarolli, Sundheim, Covell & Tummino LLP (57) ABSTRACT

Treatment of heart failure in a patient by electrically modulating both the sympathetic and parasympathetic autonomic cardiac nerve fibers that innervate the patient's heart at an extravascular site in the pericardial space of the heart. The extravascular site is any suitable single location inside the chest cavity that carries both sympathetic and parasympathetic cardiac nerves such as the cardiac plexus or the pericardial transverse sinus or any two separate extravascular sites with one site carrying predominantly sympathetic cardiac nerves and the other site carrying predominantly parasympathetic cardiac nerves for electrically modulating the balance of autonomic cardiac nerve control. Physiologic inputs from a neuromodulation system's own sensors or from separate implanted or external cardiovascular hemodynamic sensor systems can be used for closed loop control over the balance of sympathetic and parasympathetic cardiac autonomic effects on the patient's cardiac function in real time response to chronic and transient physiologic needs.

26 Claims, 10 Drawing Sheets

EXTRAVASCULAR NEUROMODULATION TO TREAT HEART FAILURE

RELATED APPLICATIONS

This application claims the benefit of U.S. Provisional Application Ser. Nos. 61/446,708 filed on 25 Feb. 2011 and 61/513,373 filed 29 Jul. 2011, which are incorporated by reference herein.

TECHNICAL FIELD

The present invention relates to the treatment of heart failure by electrical neuromodulation.

BACKGROUND

There are various options for the treatment of heart failure, including pharmacological treatment, coronary revascularization and mitral valve surgery, and devices such as pacemakers, including cardiac resynchronization therapy, or ventricular assist devices. Therapies aimed at primarily slowing the heart rate down have all been used effectively to stabilize patients in New York Heart Association (NYHA) Class II and III heart failure, decreasing morbidity and mortality and prolonging the progression to more severe heart failure. These include vagus nerve electrical stimulation and pharmacologic agents such as Beta sympathetic adrenergic blockers or ivabradine (a selective inhibitor of the $I_f$ current in the sinoatrial node without inotropic effects).

One pharmacological treatment option now reserved primarily for severe heart failure is the use of inotropic agents, such as dopamine and dobutamine. When the diseased ventricle has sufficient reserve capacity, this therapy can be very effective for increasing cardiac output. However, inotropic agents have both chronotropic (increase in heart rate) and inotropic (increase in ventricular contraction) effects. The chronotropic effect may be undesirable in patients in end stage heart failure because the rise in heart rate increases myocardial oxygen consumption. These patients have very limited reserve capacity to increase cardiac output at the expense of increasing myocardial oxygen demands. As a result, although these inotropic agents are used to increase myocardial contractility and improve hemodynamics in cases of acute and severe heart failure, clinical trials have consistently demonstrated an association between the use of inotropes and increased myocardial ischemia, arrhythmias and an increased risk of mortality. As such, there is a need for additional therapeutic regimes for the treatment of end stage heart failure that improves cardiac output without causing these undesirable effects on heart rate and myocardial oxygen consumption.

SUMMARY

The present invention discloses using electrical neuromodulation at an extravascular site to simultaneously control the balance of sympathetic (stimulatory) and parasympathetic (inhibitory) autonomic control of heart rate and contractility for the treatment of heart failure. In an embodiment, the present invention provides a method of medical treatment comprising electrical stimulation at a single extravascular site inside the chest cavity within the pericardial space on the surface of the heart (epicardial) or great vessels (epivascular) that carries both sympathetic and parasympathetic cardiac nerves (e.g., at the cardiac plexus or the pericardial transverse sinus) for electrically modulating the balance of autonomic cardiac nerve effects on cardiac function.

In another embodiment, the present invention provides a medical treatment comprising electrical stimulation at any two extravascular sites inside the chest cavity within the pericardial space on the surface of the heart (epicardium) or great vessels (epivascular) with one carrying predominantly sympathetic cardiac nerves and the other predominantly parasympathetic cardiac nerves for electrically modulating the balance of autonomic cardiac nerve effects on cardiac function.

In another embodiment, the present invention provides a device delivery method comprising a minimally invasive delivery of epivascular stimulating electrodes into the pericardium via making a subxiphoid puncture and inserting the electrode(s) through the subxiphoid puncture, or through a mini-thoracotomy.

In another embodiment, the present invention provides a neuromodulation system comprising a device comprising either an external or implanted closed loop neuromodulation controller that receives physiologic inputs from the neuromodulation system's own cardiovascular hemodynamic sensors or from separate implanted or external cardiovascular hemodynamic sensor systems and uses this information to determine the patient's current physiologic status and to optimize the cardiac autonomic nerve stimulation parameters and configurations of the embodiments listed above. This in turn optimizes the balance of sympathetic and parasympathetic cardiac autonomic effects that the extravascular electrical stimulation has on the patient's cardiac function in a real time response to chronic and transient physiologic needs.

DETAILED DESCRIPTION

Figure 1:
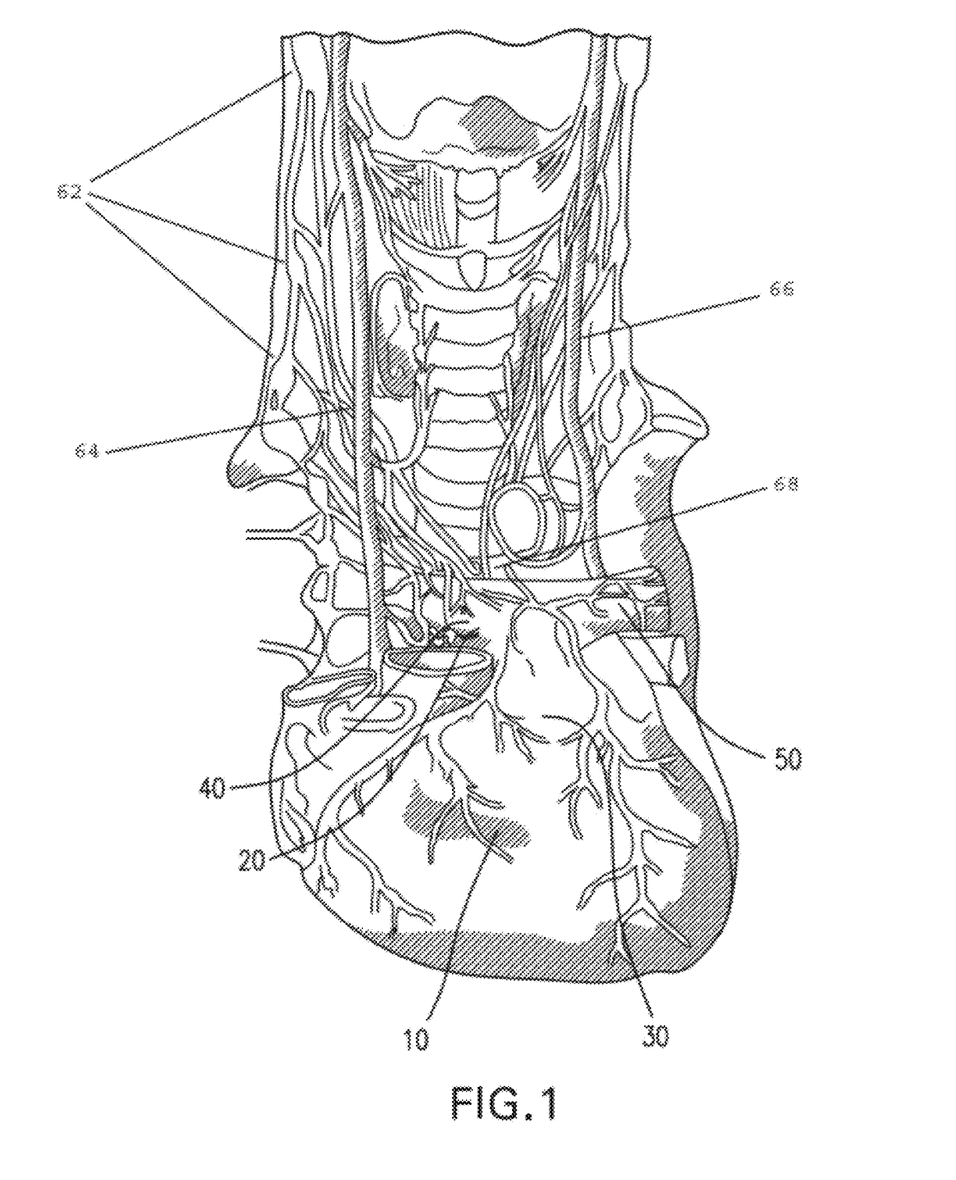
FIG. 1 shows an illustration of the typical human anatomy around the heart.

The present invention discloses treating heart failure in a patient by extravascular electrical modulation of both the sympathetic and parasympathetic cardiac nerve fibers that innervate the patient's heart. The patient is any mammalian patient and is preferably a human patient. The heart failure as used above may be acute or chronic and can be either NYHA Class II, III or IV. FIG. 1 is an illustration of the typical human anatomy of the heart 10 and the great vessels, pulmonary artery, and the aorta. Also labeled are the right sympathetic paravertebral ganglia 62, right vagus nerve 64, left vagus nerve 66, and cardiac plexus 68. The pulmonary artery 20 includes the pulmonary trunk 30, which begins at the base of the right ventricle; the right pulmonary artery 40; and the left pulmonary artery 50.

Figure 2:
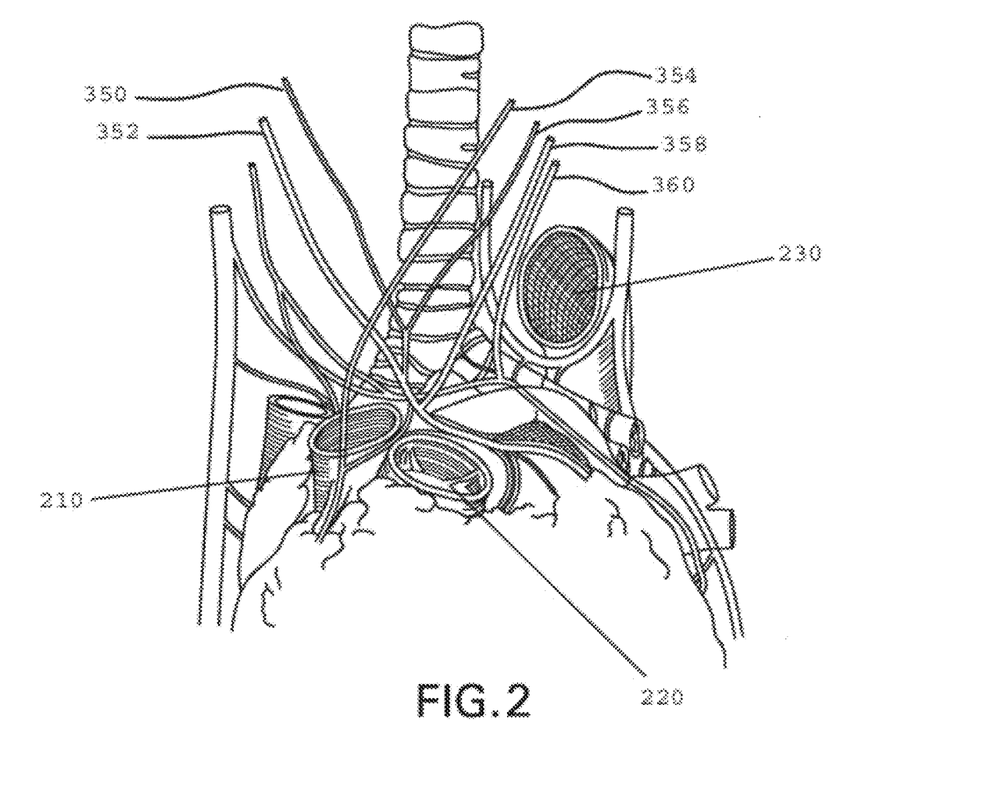
FIG. 2 shows an illustration of the typical anatomy of the sympathetic cardiopulmonary nerve fibers and the parasympathetic vagus nerve branches.

The autonomic cardiac nerve fibers that innervate the heart include parasympathetic and the sympathetic nerve trunks and ganglia. Activation of the sympathetic cardiac nerve fibers can lead to an increase in heart rate, ventricular contractility, and coronary blood flow. Activation of the parasympathetic cardiac nerves leads primarily to a decrease in heart rate only. FIG. 2 shows an illustration of the typical anatomy of the sympathetic cardiac fibers, which are located under the aortic arch between the aortic root 210 and the descending aorta 230 and in front of the pulmonary artery 220. The sympathetic fibers include the right sympathetic cardiopulmonary nerves and the left sympathetic cardiopulmonary nerves. The right sympathetic cardiopulmonary nerves include the right dorsal medial cardiopulmonary nerve 350 and the right dorsal lateral cardiopulmonary nerve 352. The left sympathetic cardiopulmonary nerves include the left ventral cardiopulmonary nerve 354, the left dorsal medial cardiopulmonary nerve 356, the left dorsal lateral cardiopulmonary nerve 358, and the left stellate cardiopulmonary nerve 360. The parasympathetic cardiac nerves arise from the superior and inferior cardiac branches of the right and left vagus nerves. The superior cardiac branches are two or three in number, and arise from the right and left vagus nerves at the upper and lower parts of the neck. The inferior cardiac branches arise from the trunk of the right vagus nerve and its recurrent nerve branch as it lies by the side of the trachea. They also arise from the recurrent nerve branch of the left vagus nerve.

As opposed to stimulation of only one arm of the cardiac autonomic system by use of a nerve cuff electrode on either a parasympathetic or sympathetic large cardiac autonomic nerve isolated from surrounding tissues, according to embodiments of the present invention, an electrode pair or preferably an array of electrodes is positioned at an extravascular site (i.e., outside of a blood vessel) to apply an electrical signal to cardiac tissues which contain both sympathetic and parasympathetic cardiac nerve fibers and ganglia. As cardiac sympathetic and parasympathetic autonomic nerve fibers frequently traverse the same outer surfaces of the heart (i.e., epicardial) and the outer surfaces of the great vessels (i.e. epivascular), electrical neuromodulation from an extravascular site may require less voltage and/or current, as compared to electrical neuromodulation from an intravascularly-placed electrode, as well as provide better control over positioning and/or orientation of the electrode to the targeted cardiac nerves.

Figure 3:
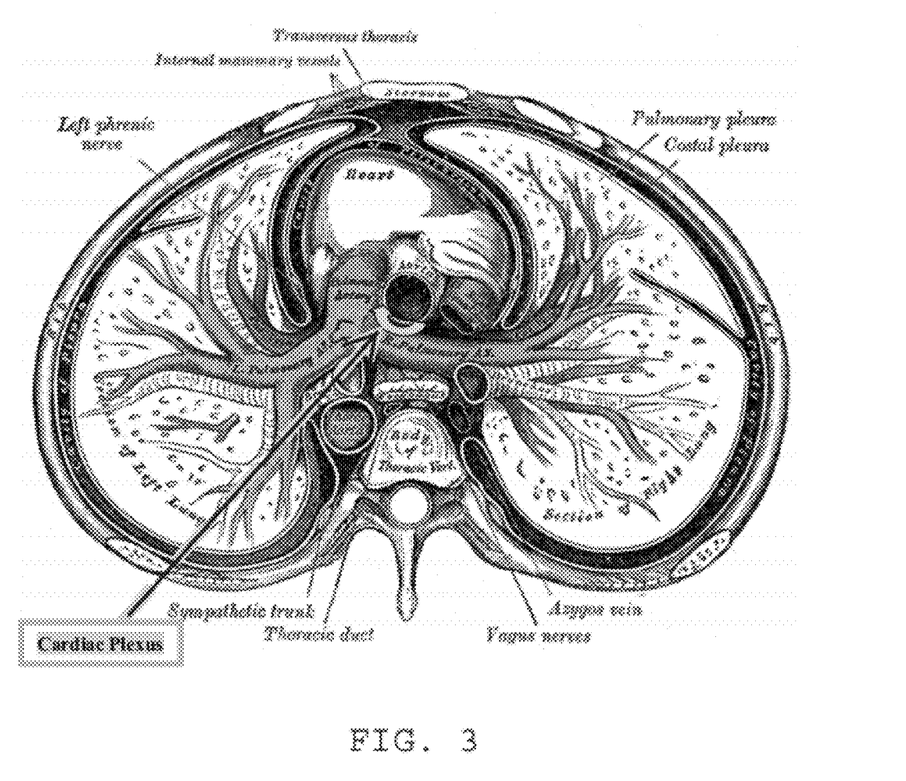
FIG. 3 shows the anatomical location of the cardiac plexus.
Figure 4:
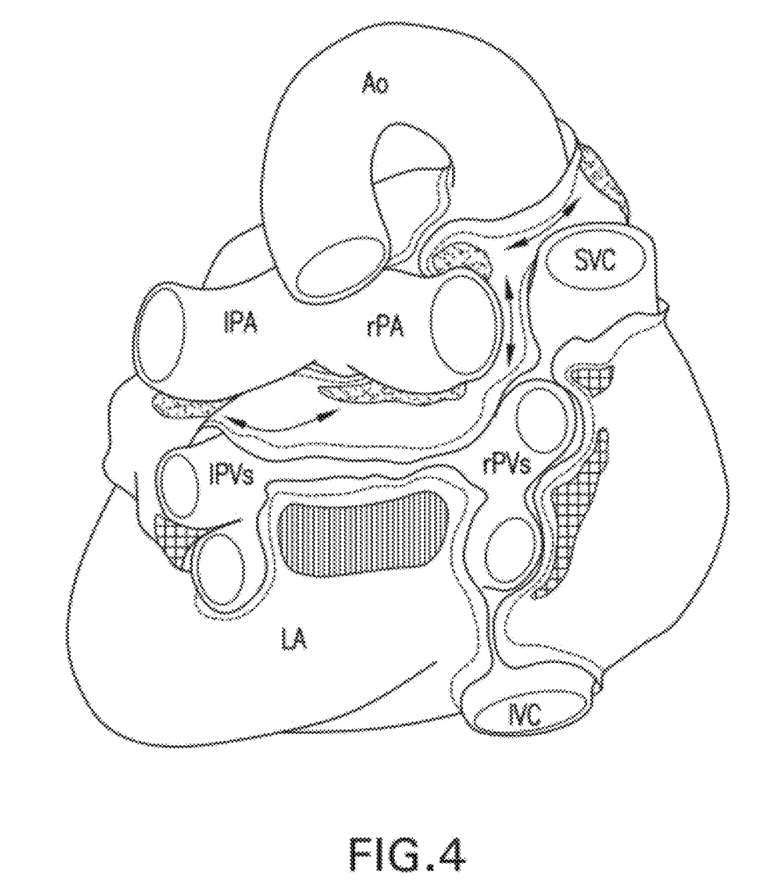
FIG. 4 shows the anatomical location of the transverse pericardial sinus and cardiac plexus.

The extravascular site may be any suitable location inside the chest cavity for electrically modulating both the sympathetic and parasympathetic autonomic cardiac fibers that innervate the heart. For example, the extravascular site may be on the epivascular surface of the great vessels, such as between the pulmonary artery and the aortic root or more specifically at the cardiac plexus as defined above and as shown in FIG. 3 (see arrow). In some cases, the extravascular site may be the pericardial transverse sinus, which is a passage within the pericardial sac that is behind and between the aortic root and pulmonary trunk and in front of the superior vena cava (see FIG. 4 showing a view of the transverse pericardial sinus from the back of the heart; Ao is the aorta, SVC is the superior vena cava, rPA is the right pulmonary artery, lPA is the left pulmonary artery, rPVs is the right pulmonary veins, lPVs is the left pulmonary veins, LA is the left atrium, and IVC is the inferior vena cava). In some cases, the extravascular site may be on the external surface of the heart (epicardial).

Electrical neuromodulation from an extravascular location containing both sympathetic and parasympathetic cardiac nerves can allow for controlling the balance of sympathetic (stimulatory) vs. parasympathetic (inhibitory) autonomic stimulation to the heart by selecting specific electrodes to be activated from an array of electrodes covering a selected extravascular site. This selection process can be driven by the current state of the patient's disease process and their current physiologic needs. For example, in earlier stage heart failure, a parasympathetic dominated neuromodulation would primarily decrease heart rate. In later stages of heart failure, where an augmentation of resting cardiac output or cardiac output during minimal exercise is needed, this may require a combination of sympathetic stimulation to increase contractility and parasympathetic stimulation to minimize the increase in heart rate normally seen with sympathetic stimulation. This selective neuromodulation that preferentially affects ventricular contractility more than heart rate produces the positive inotropic effect of an inotropic drug without the adverse effect of significantly increased myocardial oxygen demand in a diseased heart.

Figure 5:
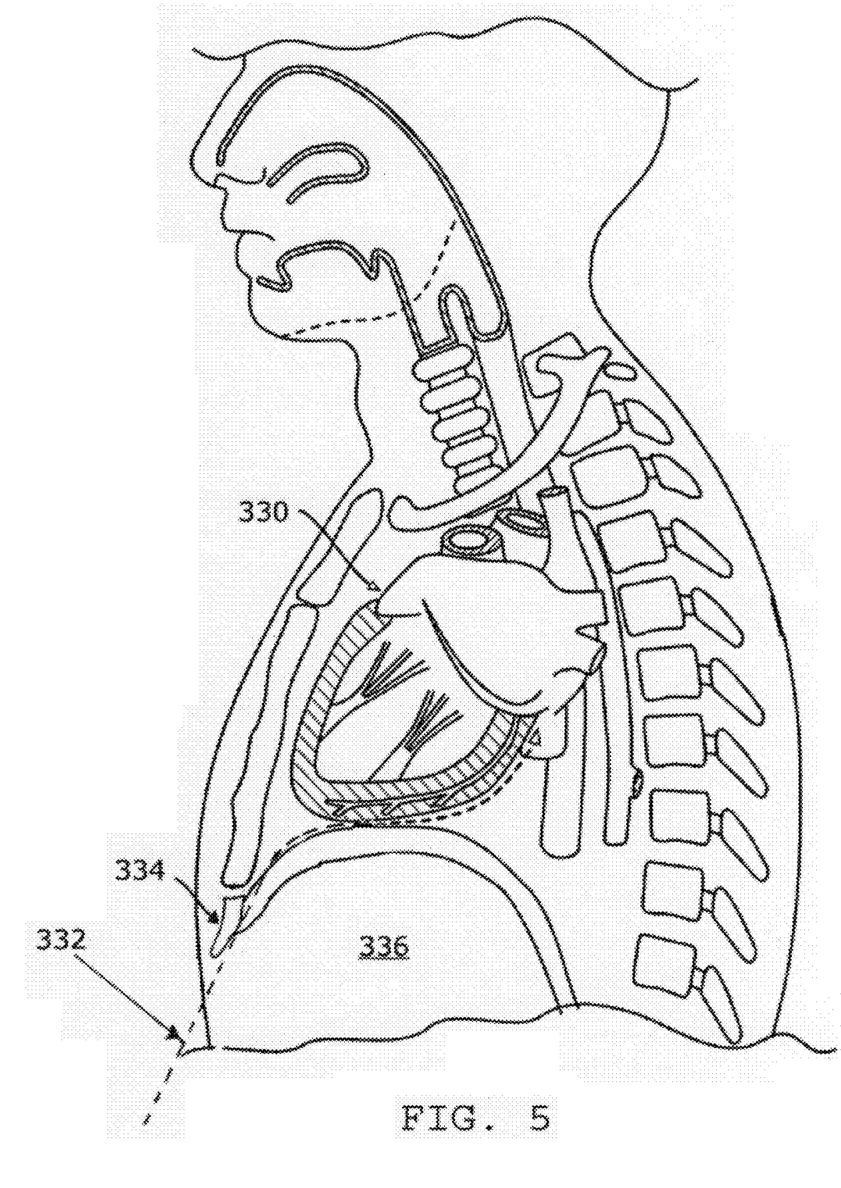
FIG. 5 shows a side view of the chest anatomy to demonstrate a subxiphoid pericardial access route.
Figure 6A:
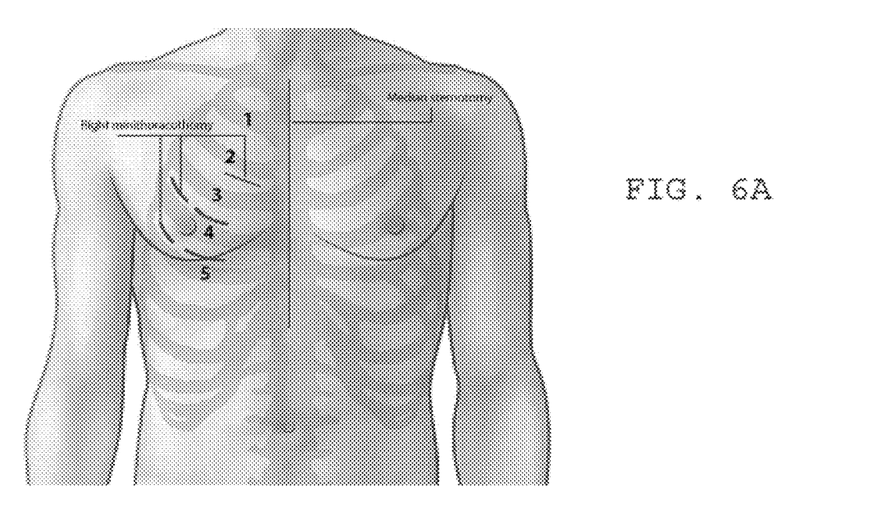
FIGS. 6A and 6B show a mini-thoracotomy pericardial access.
Figure 6B:
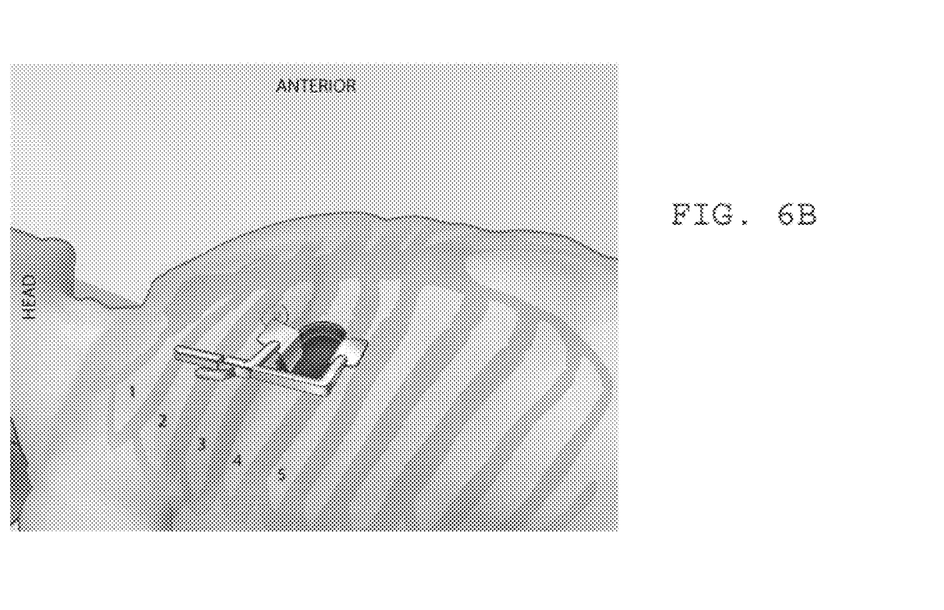

Any suitable access route may be used to deliver the electrode to the extravascular site. In certain embodiments, the access route is through the pericardial space of the heart. Pericardial access may be provided in any suitable way. One particular example is a subxiphoid approach as illustrated in FIG. 5 and described in U.S. Pat. No. 7,247,134 (Vidlund et al.), which is incorporated by reference herein. In this approach, a hollow bore needle is inserted into the chest cavity by a percutaneous puncture 332 below the xiphoid 334. A guidewire can be inserted through the hollow needle towards the cardiac space. The needle is then removed leaving the guidewire in place. Dilators may then be advanced over the guidewire to provide a pathway to the cardiac space. The electrode may then be inserted through this pathway over the abdomen 336 and into the pericardium of the heart 330. Once in the pericardium, the electrode may be advanced through the pericardial space to the target site. The electrode may be secured at the target site (e.g., by sutures) or it may be left free so that it can be easily withdrawn. Positioning of the electrode to its target site may be guided by any suitable imaging technique, including fluoroscopy or echocardiography. A second example of possible pericardial access is a mini-thoracotomy as illustrated in FIGS. 6A and 6B (the numerals refer to the ribs), where a much smaller opening through the thoracic chest wall is used for electrode placement than is typically done for most full thoracotomy cardiac surgical procedures where full access to the heart is needed. FIG. 6A shows mini-thoracotomy incisions in the second, third, and fourth intercostal spaces. FIG. 6B shows a mini-thoracotomy access provided by a rib retractor placed in the fourth intercostal space.

The electrode used for delivering the electrical signal may be any electrode suitable for use at an extravascular location inside the chest cavity. The design characteristics of the electrode will vary depending upon the needs of the particular application, including such features as the number, direction, position, and/or arrangement of electrode contacts on the electrode; number of independent channels; and geometry and/or configuration of the electrode. Stimulation of extravascular tissues carrying many cardiac nerve fibers that are not visible to the eye for direct stimulation may require an array of electrodes to determine the optimum anode(s) and cathode(s) to be used for producing the optimum desired cardiovascular effect. For extravascular tissues such as the cardiac plexus containing both sympathetic and parasympathetic nerve fibers and ganglia, an electrode array can be used to select the desired balance of sympathetic and parasympathetic cardiac stimulation.

Figure 7:
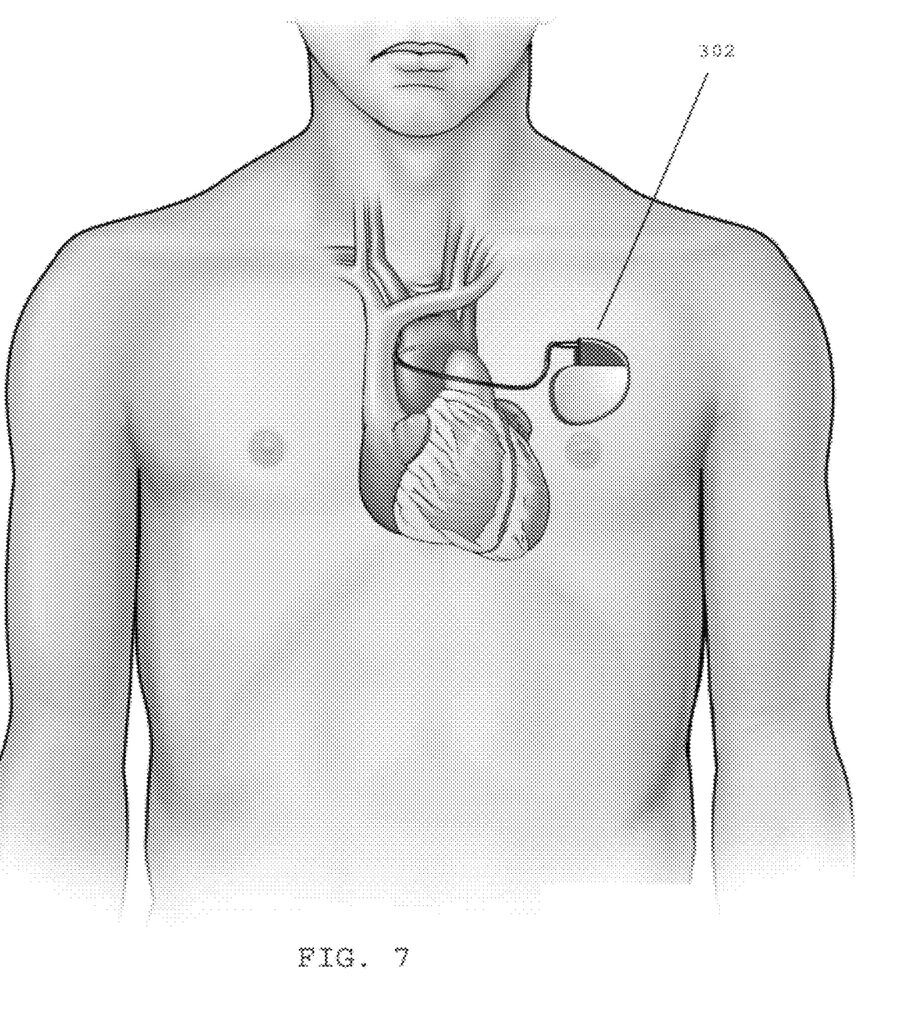
FIG. 7 shows an implanted neuromodulation pulse generator system integral with the stimulation lead.

The present invention may also be embodied as a neuromodulation system that includes an electrode and a controller that operates and/or supplies electrical power to the electrode for delivering an electrical signal to the autonomic cardiac nerve fibers. The controller may be designed for implantation or for placement external to the patient's body. The controller may also be integral with the electrode (such as a combined stimulation lead and pulse generator system 302 as shown in FIG. 7). The electrode may be connected to the controller by any suitable means, including the use of wires, leads, and/or catheters. The external controller may be powered by a battery (which can be rechargeable) or an external power supply. The implanted controller may be powered by a battery which can be recharged through a transcutaneous energy transfer system (TETS).

The controller may be programmed to adjust various parameters of the electrical signal, including pulse width, frequency, voltage, current amplitude, duration, pulse train length, and/or pulse waveform. Such parameters will vary depending upon the particular application and site of stimulation. Higher energy levels are needed for stimulation of cardiac nerve fibers within extravascular tissues vs. that required for direct nerve stimulations. For example, the voltage may be selected from a range of 0.1 to 50 V, pulse width may be selected from a range of 100-10,000 µs per phase, average pulse frequency may be selected from a range of 2-200 Hz, and current may be selected from a range of 0.1 µA-30 mA. Programming may also include activation or deactivation of individual or combinations of electrodes within an electrode array and the selection of the direction of the current by selecting which activated electrode(s) are to act as the anode vs. the cathode.

The electrical signal may be monophasic, biphasic, multiphasic, etc. The controller may be programmed to be unipolar, defined as the flow of current from a stimulating electrode(s) at the site of desired nerve stimulation to a reference ground with a larger surface area distant from the stimulation site, frequently the body of the stimulator; or bipolar stimulation where the stimulating current flows between closely spaced anode and cathode electrodes frequently lying on the same catheter. The electrical signal may be current-controlled, voltage-controlled, or a combination of both. The electrical signal may be pulsatile, episodic, continuous, cyclic, phasic, in clusters, intermittent, upon demand by a user, or preprogrammed to respond to a sensor. The controller may operate any number or combination of electrodes and may make any electrode in an electrode array either an anode or cathode depending on the application and biologic response.

In certain embodiments, the neuromodulation system includes a feedback mechanism for adjusting the electrical signal based on one or more of the patient's cardiovascular parameters. For this purpose, the neuromodulation system may sense heart rate via the stimulating electrodes or further include a sensor(s) for measuring a patient's cardiovascular parameter. Information about the cardiovascular parameter is fed to the controller, which is programmed to adjust the stimulation signal being applied to the electrode in response to the information about the cardiovascular parameter. Additional non-limiting sources of cardiovascular parameter feedback to the neuromodulator system include sensed physiologic parameter input from an implanted pacemaker and inputs from a separate implanted or external physiologic monitor which receives its inputs from physiologic sensors. Sensor inputs to the neuromodulation system can be via either hardwired or radio frequency telemetry.

Non-limiting examples of cardiovascular parameters that may be used for the feedback mechanism include systemic and pulmonary arterial blood pressure, intracardiac chamber pressures, central venous pressure, capillary pressure, systolic pressure variation, pulmonary artery wedge pressure, cardiac output, systemic vascular resistance, arterial blood gases and mixed venous oxygen saturation. These cardiovascular parameters can be monitored by a variety of methods or devices, including electrocardiography, pacemaker-based cardiac rhythm information and activity level sensors, invasive hemodynamics, implantable intracardiac pressure measurement devices, echocardiography, peripheral blood pressure measurement, continuous cardiac output measurement devices or other techniques or devices known in the art to measure cardiovascular hemodynamics. In some cases, the various types of cardiovascular parameters may be employed together in any combination.

Figure 8:
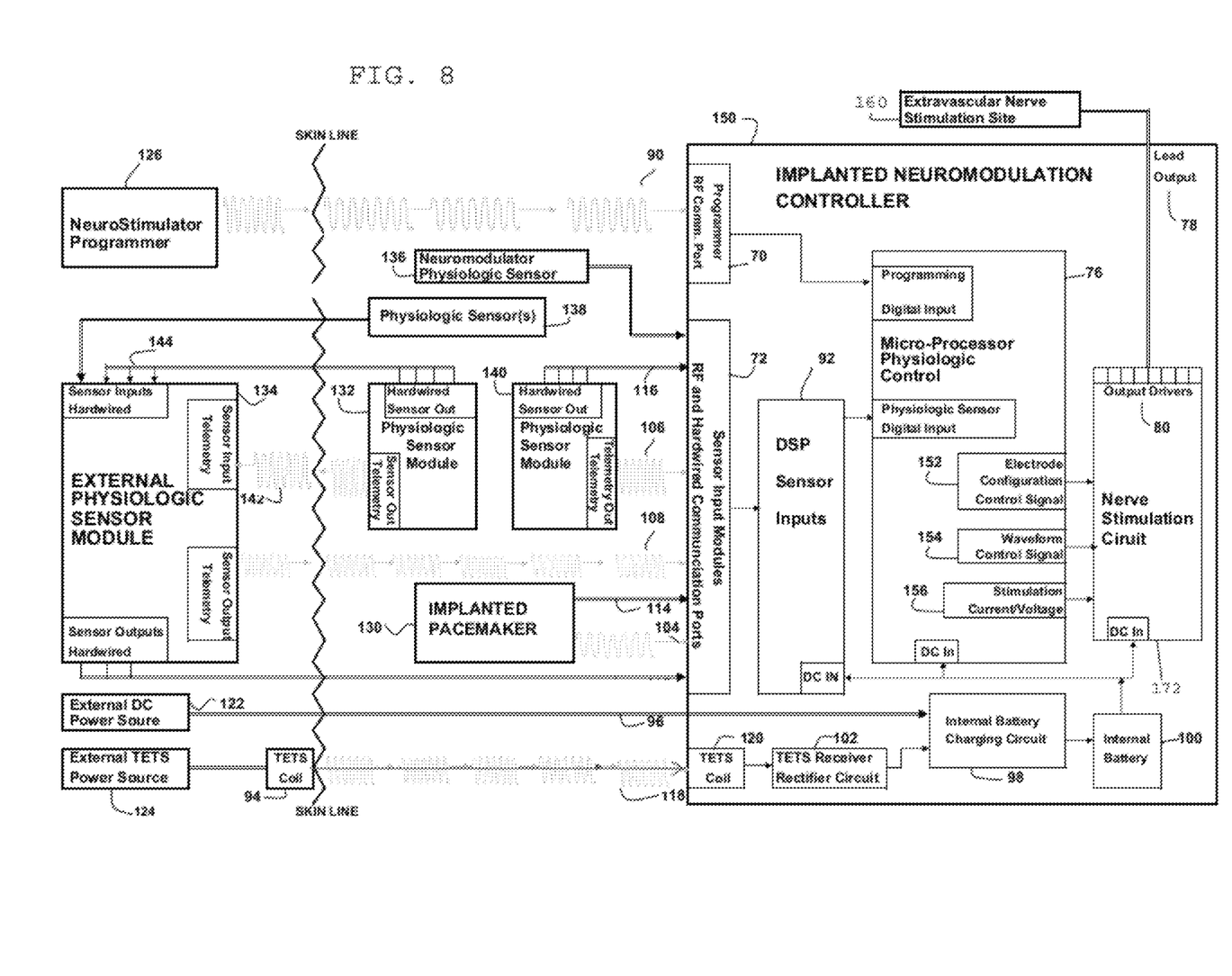
FIG. 8 shows a block diagram of an implanted controller in an embodiment of the present invention.

FIG. 8 shows an illustration of a non-limiting example of an implanted neuromodulation controller 150 comprising an radio frequency communications port 70 to receive incoming operational and patient specific controller programming, hardwired and or radio frequency communication port(s) 72 to receive incoming physiologic sensor inputs from either the neuromodulation controllers dedicated physiologic sensors 136, an implanted pacemaker 130, an implanted physiologic sensor module 140 or an external physiologic sensor module 134, a digital signal processor 92 for signal conditioning and filtering, a microprocessor 76 to receive programming and sensor inputs, implement the closed loop control algorithm and to output control signals to the nerve stimulation circuit 172 which outputs stimulation pulses to selected output drivers 80 that activate selected electrodes within the stimulation catheter 78. Controller programming inputs 90 are from an external programmer 126 via radio frequency communication. Controller power inputs are either via hardwired DC power leads 96 from an external DC power supply 122 or via radio frequency TETS 118 consisting of an external TETS power oscillator 124 to a skin mounted primary coil 94 to a secondary coil within the implanted controller 120. TETS radio frequency input to the secondary coil is rectified to a DC supply 102 which is input to a battery charging circuit 98. Percutaneous DC power leads 96 also supply the battery charging circuit 98. The battery charging circuit charges the controller internal battery 100 which provides power to all electronics and the stimulation output drivers in the controller. Physiologic sensor inputs to the controller can be obtained from either the controller's own integrated physiologic sensor 136 and or any combination of the following; radio frequency 104 or hardwired 114 sensor inputs from an implanted pacemaker 130, radio frequency 106 or hardwired 116 inputs from an implanted physiologic sensor module(s) 140, or radio frequency 108 or hardwired 118 inputs from an external physiologic sensor module(s) 134. The external physiologic sensor module 134 can receive multiple sensor inputs from its own physiologic sensors 138 or from an implanted physiologic sensor module 132 via radio frequency 142 or hardwired 144 communication.

In operation, information from the physiologic sensors is received at the implanted neuromodulation controller via the radio frequency and or hardwired communication ports 72. The analog or digital signal(s) from the sensor is converted to digital form and conditioned through digital signal processor (DSP) 92. Microprocessor 76 receives the sensor inputs from the DSP 92 and operational programming information for the Programmer Radio Frequency Communication port 70. It uses this information in an algorithm to analyze the cardiovascular parameter of the patient. Microprocessor 76 then outputs instructions to the Nerve Stimulation Circuit 72, which generates the electrical signal to be applied to the electrode. Microprocessor 76 may instruct the electrode configuration to be activated and choice of anode vs. cathode 152, the stimulating waveform configuration determining the frequency, pulse width and duty cycle 154 and the stimulation amplitude 156 defined as an applied voltage or current depending on the configuration of the stimulator for voltage or current control. The electrical control signals are converted to the stimulation waveforms delivered through output drivers 80 to the selected electrode wires within the extravascular lead 78 which is applied to the extravascular stimulation site 156.

Figure 9:
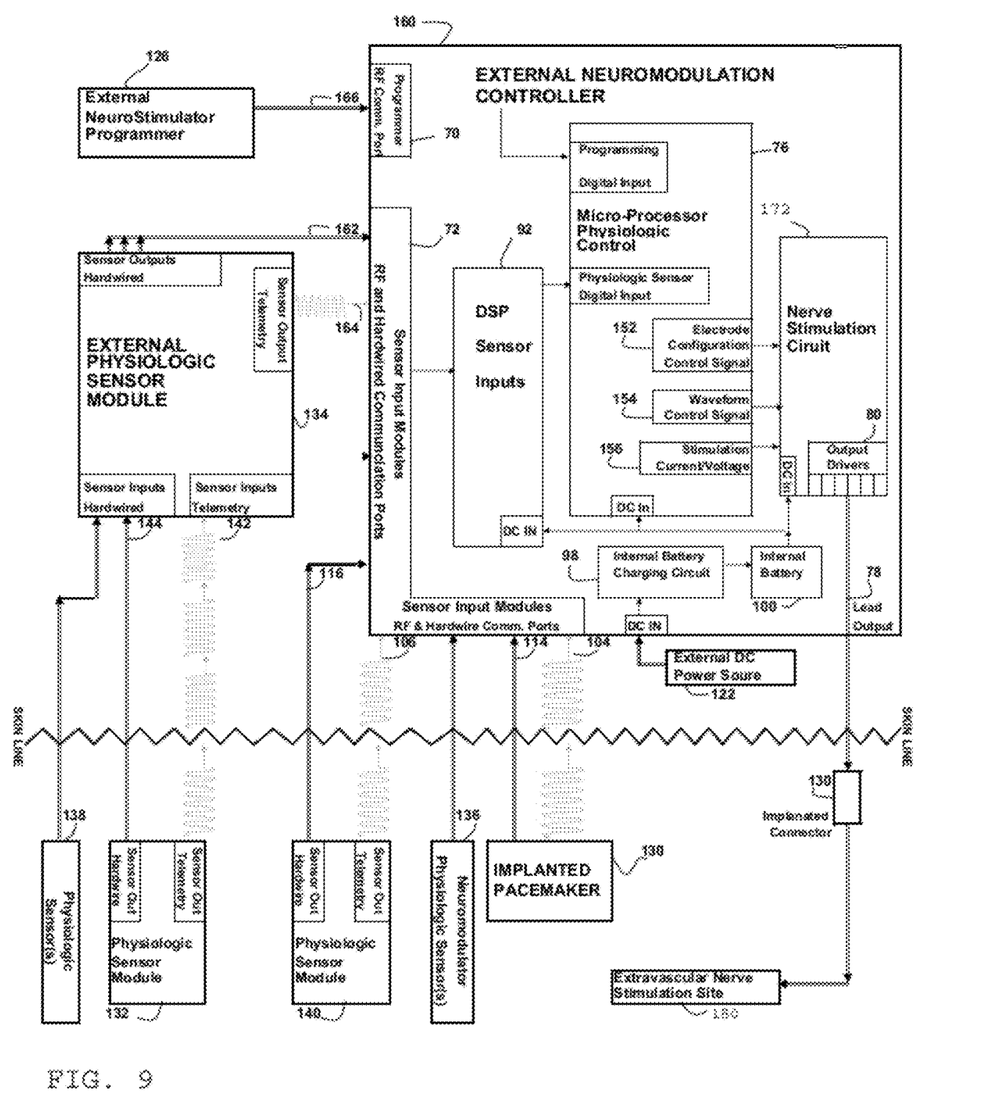
FIG. 9 shows a block diagram of an external controller in an embodiment of the present invention.

FIG. 9 shows an illustration of a non-limiting example of an external neuromodulation controller 160 comprising a hardwired communications port 70 to receive incoming operational and patient specific controller programming, hardwired and or radio frequency communication port(s) 72 to receive incoming physiologic sensor inputs from either the neuromodulation controllers dedicated physiologic sensor(s) 136, an implanted pacemaker 130, an implanted physiologic sensor module 140 or an external physiologic sensor module 134, a digital signal processor 92 for signal conditioning and filtering, a microprocessor 76 to receive programming and sensor inputs, implement the closed loop control algorithm and to output control signals to the nerve stimulation circuit 172 which outputs stimulation pulses to selected output drivers 80 that activate selected electrodes within the stimulation lead 78. An implanted connector 130 can be used to leave the implanted extravascular electrode array and lead subcutaneously so that the external neuromodulation controller can be used at a later date by subcutaneous cut down as needed. Controller programming inputs 166 are from an external programmer 126 via hardwired communication. Controller power input is from an external DC power supply 122 which is input to a battery charging circuit 98. The battery charging circuit charges the controller internal battery 100 which provides power to all electronics and the stimulation output drivers in the controller. Physiologic sensor inputs to the controller can be obtained from either the controller's own integrated physiologic sensor 136 and or any combination of the following; radio frequency 104 or hardwired 114 sensor inputs from an implanted pacemaker 130, radio frequency 106 or hardwired 116 inputs from an implanted physiologic sensor module(s) 140, or radio frequency 164 or hardwired 162 inputs from an external physiologic sensor module(s) 134. The external physiologic sensor module 134 can receive multiple sensor inputs from its own physiologic sensors 138 or from an implanted physiologic sensor module 132 via radio frequency 142 or hardwired 144 communications.

In operation, information from the physiologic sensors is received at the explanted neuromodulation controller via the radio frequency and or hardwired communication ports 72. The analog or digital signal(s) from the sensor is converted to digital form and conditioned through digital signal processor (DSP) 92. Microprocessor 76 receives the sensor inputs from the DSP 92 and operational programming information for the Programmer Radio Frequency Communication port 70. It uses this information in an algorithm to analyze the cardiovascular parameter of the patient. Microprocessor 76 then outputs instructions to the Nerve Stimulation Circuit 172, which generates the electrical signal to be applied to the electrode. Microprocessor 76 may instruct the electrode configuration to be activated and choice of anode vs. cathode 152, the stimulating waveform configuration determining the frequency, pulse width and duty cycle 154 and the stimulation amplitude 156 defined as an applied voltage or current depending on the configuration of the stimulator for voltage or current control. The electrical control signals are converted to the stimulation waveforms delivered through output drivers 80 to the selected electrode wires within the extravascular lead 78 which is applied to the extravascular stimulation site 180 via an implanted subcutaneous lead connector 130.

Figure 10:
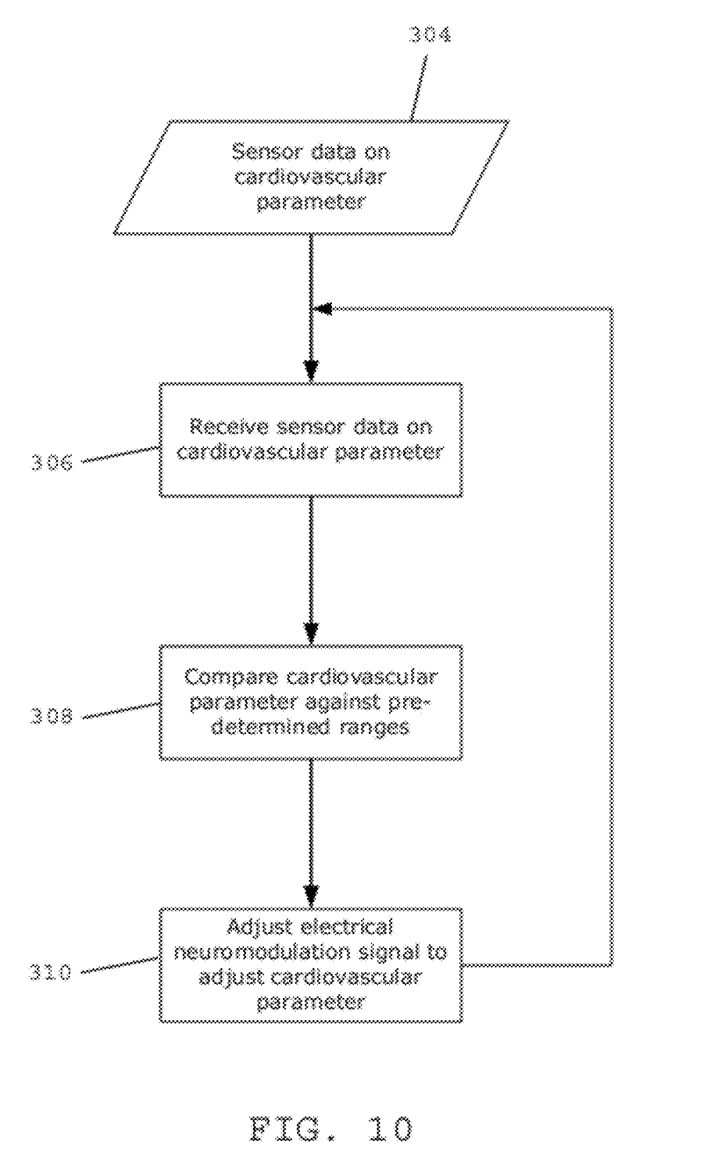
FIG. 10 shows a flow diagram of a feedback control algorithm that can be used by the neuromodulation controller.

FIG. 10 shows an example feedback control algorithm that can be used in the present invention. The algorithm receives data for the cardiovascular parameter from the sensor (in steps 304 and 306). Next, the algorithm compares the cardiovascular parameter to a pre-determined range of values in step 308. Based on this comparison, the algorithm adjusts the extravascular cardiac autonomic nerve stimulation in order to modulate the cardiovascular response in step 310. This can be done by altering the stimulation parameters such as the stimulus frequency or energy level or by selecting or changing the anode and cathode electrodes to activate for stimulation. For example, if the algorithm determines that cardiac output is too low in an ischemic heart failure patient, it may make adjustments to the stimulation parameters to increase cardiac contractility while limiting the increase in heart rate in order to increase the cardiac output while limiting myocardial oxygen demand. The adjustment process may be implemented using any suitable control technique, including proportional-integral-derivative (PID) algorithms or fuzzy logic rules. The gains and weighting factors used in a PID controller can be determined by the clinician's programmable inputs on the patient's individual cardiac status such as; degree of heart failure, cardiac output reserve during increased physiologic demand, degree of ischemic heart disease, resting heart rate, systemic vascular resistance, arrhythmia status and right heart function. This will allow the clinician to individualize extravascular cardiac autonomic nerve stimulation for both chronic heart failure therapy and for a safe and effective transient response in these patients to any sensed increase in physiologic demand. An example would be the neuromodulation controller receiving sensory input(s) indicating mild exercise such as a decrease in mixed venous oxygen levels and an increase in heart rate, left heart chamber pressures and activity level. This sensory feedback would result in a change in stimulation parameters which results in an increase in cardiac output that is proportional to that patient's degree of heart failure, type of heart failure and their cardiac reserve status.

EXAMPLES

Experiments for extravascular stimulation of cardiac nerves were performed on 12 dogs. After opening the chests under general anesthesia, a stimulating catheter electrode was placed epivascularly in the area know as the cardiac plexus near the right pulmonary artery behind the ascending aorta. An electrical signal was provided to the electrode with the stimulation frequency set at 20 Hz, the pulse width set at 4 msec, and the voltage ranging between 10-50 V. Hemodynamic and epicardial echocardiographic data were recorded with and without stimulation using a left ventricular conductance catheter, Swan-Ganz catheter, and left atrial pressure line.

In all 12 dogs, the systolic aortic and systolic left ventricular pressures, its dP/dt, and left ventricular stroke work increased with stimulation ($p<0.0001$ for all the parameters) with cardiac output increasing from $2.9\pm1.0$ to $3.4\pm1.0$ L/min (p=0.001). The end-systolic elastance and preload recruitable stroke work, which are load-independent indices of left ventricular contractility, significantly increased with stimulation (from 1.2±0.4 to 1.5±0.5 mm Hg/ml, p=0.0001; and from 30.1±11.0 to 39.3±7.8 mm Hg, p=0.003, respectively), suggesting an increase in left ventricular contractility. Left ventricular ejection fraction with echocardiography significantly increased from 50.5±7.7 to 57.6±8.2% (p=0.012). Heart rate (from 101±20 to 97±21 beat/min), central venous pressure, pulmonary arterial pressure, and left atrial pressure remained unchanged (p>0.1). There was only a slight but statistically significant increase in systemic vascular resistance (from 1,426±339 to 1,574±250 dyne·sec·m$^{-5}$, p=0.04)) and a decrease in pulmonary vascular resistance (from 161±64 to 127±9 dyne·sec·m$^{-5}$, p=0.01). These results demonstrate that electrical neuromodulation of the present invention can selectively increase ventricular contractility with minimal changes in heart rate, systemic vascular resistance, and/or pulmonary vascular resistance.

The foregoing description and examples has been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method of treating heart failure in a patient in need thereof comprising:
   positioning at least one electrode on at least one extravascular site inside the patient's chest cavity; and
   applying an electrical signal to the at least one electrode to simultaneously stimulate both sympathetic and parasympathetic autonomic cardiac nerve fibers that innervate the heart to treat the heart failure, wherein the at least one extravascular site is confirmed as carrying predominantly sympathetic cardiac autonomic nerves or parasympathetic cardiac autonomic nerves during implantation by either a predominately inotropic and positive chronotropic effect for the sympathetic dominant areas of stimulation or a predominately negative chronotropic effect for the parasympathetic dominant areas of stimulation.

2. The method of claim 1, wherein the at least one extravascular site is two extravascular sites.

3. The method of claim 1, wherein the at least one extravascular site is an epicardial surface or an epivascular surface.

4. The method of claim 1, wherein the at least one electrode is a single electrode, a single electrode array, or a plurality of electrode arrays.

5. The method of claim 4, wherein selection of the at least one electrode depends at least upon the size of the epivascular or epicardial surface area to be stimulated and the spatial resolution of the sympathetic and or parasympathetic nerves traversing the selected surface for stimulation.

6. The method of claim 3, wherein the at least one electrode is an electrode array and further comprising varying at least one of the following: the number, direction, position, and/or arrangement of electrodes; the selection of electrodes to be activated or inactivated in the electrode array; the spatial configuration of the active electrodes in the electrode array; and the direction of stimulating current based on an electrode or electrodes from the electrode array selected to be an anode or cathode.

7. The method of claim 1, wherein the at least one extravascular site is a single extravascular site containing both parasympathetic and sympathetic cardiac autonomic nerves and the at least one electrode is a single electrode array.

8. The method of claim 1, wherein the at least one extravascular site is two different extravascular sites and the at least one electrode is two different electrode arrays and further comprising stimulating one site containing predominantly parasympathetic cardiac autonomic nerves with one electrode array and stimulating another site containing primarily sympathetic cardiac autonomic nerves with the other electrode array.

9. The method of claim 1, wherein the at least one extravascular site is either the cardiac plexus or the pericardial transverse sinus.

10. The method of claim 2, wherein the two extravascular sites are in the pericardial space of the heart which stimulates areas on the surface of the heart or the great vessels, or at the pericardial transverse sinus which carries either predominately sympathetic or predominately parasympathetic cardiac autonomic nerves.

11. The method of claim 1, further comprising inserting the at least one electrode into the pericardial space and advancing the at least one electrode through the pericardial space to the at least one extravascular site.

12. The method of claim 11, further comprising either making a subxiphoid puncture and inserting the at least one electrode(s) through the subxiphoid puncture or inserting the at least one electrode through a mini-thoracotomy.

13. The method of claim 11, wherein the positioning of the at least one electrode is guided by fluoroscopy, echocardiography or endoscopic direct visualization.

14. The method of claim 1, further comprising sensing at least one cardiovascular parameter of the patient by using a closed loop neuromodulation controller and, based on the at least one cardiovascular parameter, adjusting the electrical signal applied by the at least one electrode to alter the balance of sympathetic and parasympathetic cardiac autonomic fiber control over cardiac function.

15. The method of claim 14, wherein the at least one cardiovascular parameter is systemic or pulmonary arterial blood pressure, intracardiac chamber pressures, central venous pressure, capillary pressure, systolic pressure variation, arterial blood gases, cardiac output, systemic vascular resistance, pulmonary artery wedge pressure, mixed venous oxygen saturation, heart rate, cardiac rhythm or any other parameter to measure cardiovascular hemodynamics.

16. The method of claim 14, further comprising obtaining the at least one cardiovascular parameter from the controller own physiologic sensors or obtaining the at least one cardiovascular parameter from electrocardiography, pacemaker-based cardiac rhythm information, activity level sensors, invasive hemodynamics, implantable intracardiac pressure measurement devices, echocardiography, peripheral blood pressure measurement, continuous cardiac output measurement devices or other techniques or devices to measure cardiovascular hemodynamics.

17. The method of claim 14, wherein the at least one cardiovascular parameters is various types of cardiovascular parameters that are measured either individually or in any combination to implement a closed loop control logic.

18. The method of claim 14, wherein the closed loop neuromodulation controller is permanently implanted within the patient's body with at least one integrated implanted stimulation lead.

19. The method of claim 18, wherein the implanted neuromodulation controller receives its power via a percutaneous hardwired lead or via a transcutaneous energy transfer system comprising an external power source and oscillator, an external primary coil placed on the skin, a subcutaneously implanted secondary coil to receive power across the skin and a rectifier circuit to convert the high frequency oscillatory power to DC voltage, the DC voltage used to supply the controller's internal battery charging circuitry.

20. The method of claim 18, wherein the implanted neuromodulation controller receives physiologic sensor information from its own at least one integrated implanted sensor, from other implanted physiologic sensor modules, or from external physiologic sensor modules.

21. The method of claim 18, wherein the implanted neuromodulation controller receives its physiologic sensor feedback via hardwired input or telemetry.

22. The method of claim 18, wherein the closed loop neuromodulation controller is external to the body of the patient.

23. The method of claim 22, wherein the external closed loop neuromodulation controller is in communication with at least one percutaneous lead and a subcutaneously implanted connector which connects the at least one percutaneous lead to at least one implanted stimulation lead integrated with the external closed loop neuromodulation controller.

24. The method of claim 22, wherein the external neuromodulation controller receives physiologic sensor information from either its own integrated sensor(s) placed in or on the body, from other external physiologic sensor modules and their associated sensors, from implanted sensor modules, or from pacemakers.

25. The method of claim 22, wherein the external neuromodulation controller receives its physiologic sensor feedback via hardwired input or telemetry from physiologic sensors and sensor modules either inside or outside the patient's body.

26. The method of claim 1, wherein the at least one extravascular site is the pericardial space of the heart.

* * * * *